United States Patent [19]

Osti

[11] Patent Number: 5,433,696
[45] Date of Patent: Jul. 18, 1995

[54] CERVICAL ORTHOSIS WITH MULTIPLANAR ADJUSTMENT

[76] Inventor: Leonardo Osti, Viale Cavour 115, Ferrara, Italy

[21] Appl. No.: 166,315

[22] Filed: Dec. 10, 1993

[51] Int. Cl.⁶ .............................................. A61F 5/00
[52] U.S. Cl. ............................... 602/18; 128/DIG. 23
[58] Field of Search ................................... 602/17–19; 128/DIG. 23

[56] References Cited

U.S. PATENT DOCUMENTS

| | | | |
|---|---|---|---|
| 1,930,440 | 10/1933 | Longfellow | 602/18 |
| 2,474,200 | 6/1949 | McBee | 602/18 |
| 2,807,260 | 9/1957 | Teufel | 602/17 |
| 2,820,455 | 1/1958 | Hall | 602/18 |
| 2,828,736 | 4/1958 | Monfardini | 602/18 |
| 2,904,040 | 9/1959 | Hale | 602/18 |
| 3,177,869 | 4/1965 | Bartels | 602/18 |
| 3,364,926 | 1/1968 | Alderson | 602/18 |
| 3,504,667 | 4/1970 | McFarlane | 602/18 |
| 4,677,969 | 7/1987 | Calabrese | 602/18 |
| 4,827,915 | 5/1989 | Gorsen | 602/18 |

*Primary Examiner*—Linda C. M. Dvorak
*Attorney, Agent, or Firm*—McAulay Fisher Nissen Goldberg & Kiel

[57] ABSTRACT

A cervical orthosis having a thoracosternal semi-component for a thoracosternal position and a dorsal semi-component for a dorsal position, each of he semi-components including a lower and an upper part, a pair of upper and lower connectors for connection of the upper parts and the lower parts of the semi-components, a connector as one of the upper and the lower parts for connection of the semi-components, and spacers for spacing of the lower and upper parts of each of the semi-components frown each other to provided for the adjustment to fit each individual wearer.

20 Claims, 2 Drawing Sheets

CERVICAL ORTHOSIS WITH MULTIPLANAR ADJUSTMENT

BACKGROUND OF THE INVENTION

1. Field of the Invention

This invention relates to a cervical orthosis.

More particularly, the invention is concerned with a cervical orthosis which provides for immobilization of a patient in a position which is considered to be the best in relation to the conformation, location and size of a herniated disc segment. In particular, the largest opening width of an intervertebral space adjacent to the herniated disc segment is related to the aforesaid best position.

2. Description of the Prior Art

Overall stress of a herniated segment is decreased by opening the width of the intervertebral space proximate and next to the damaged disc so as to reduce the compression directly caused by the herniated disc segment on the disc. An intervertebral disc is formed and comprises a peripheral ring or annulus and a central structural nucleus which is interposed between two contiguous vertebral bodies and acts as a shock absorber between the two bodies. Whenever a modification or change in the intervertebral disc shape takes place, then a protrusion or a herniation of a part of the disc takes place and a compression or pressure can occur or take place on different nerve roots. This is responsible for or causes painful and/or paresthetic symptomology.

Cervical orthoses are currently used in the treatment of cervical spine injuries and in the conservative treatment of cervical disc pathology. As a conservative treatment, the cervical orthoses are used to immobilize the cervical spine in order to limit the mechanical stresses on the protruded or herniated part of the disc and to decrease the compressive action of this part on the closer nerve roots.

There are two groups of orthosis available now on the market. The first one, not regulatable or adjustable, supports and immobilizes the cervical spine in a unique position, offering only an advantage of immobilization, and a second group which is adjustable, but adjustable only on the anteposterior plane, using different devices. This is useful only when the herniated segment is centrally located. When a hernia occurs in a lateral position, either to the right or left side, the orthoses now available, insofar as I am aware, do not immobilize the cervical spine in the optimal position related to the herniated disc segment.

DESCRIPTION OF THE INVENTION

A containment apparatus for the orthosis according to the invention is preferably formed by two, front and rear, foamed plastic semi-components. These components create a stable support stabilized by four different distance spacers. The spacers can be set at variable lengths to support the upper part which embraces the mento-nuchal region in an encasing structure in order to obtain the best position for treatment. The plastic foam support structure is properly shaped to manage an anatomic support, and is assembled by setting the front and the rear semi-components, using the face as a reference for the front component and the back of the head for the rear component.

The orthosis according to the invention is provided with an adjustable connection means for connecting the semi-components together while permitting use of the orthosis on different individuals having different sized and shaped body portions.

In order that the invention will be more clearly appreciated, reference will be made to the accompanying drawings.

DETAILED DESCRIPTION OF THE PREFERRED EMBODIMENT

Figure 1:
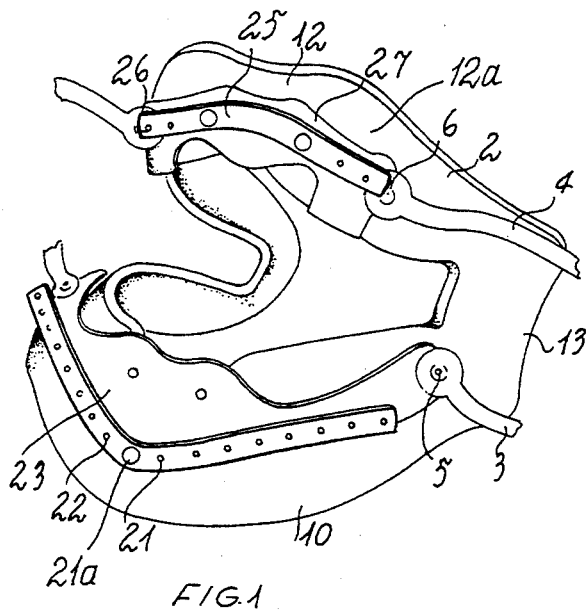
FIG. 1 is a rear perspective view of a rear part of a cervical orthosis illustrating a lower rear and upper rear component provided with a multiplanar adjustment, as viewed from the rear of an individual wearer.
Figure 2:
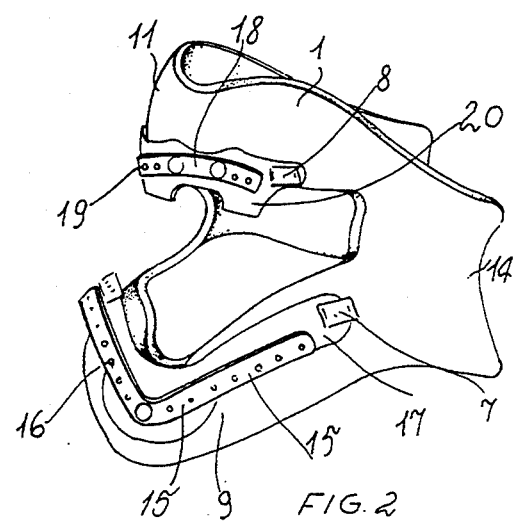
FIG. 2 is a front perspective view of a front part of a cervical orthosis illustrating a lower front and an upper front component which is combined with the rear part of the cervical orthosis as shown in FIG. 1.
Figure 3:
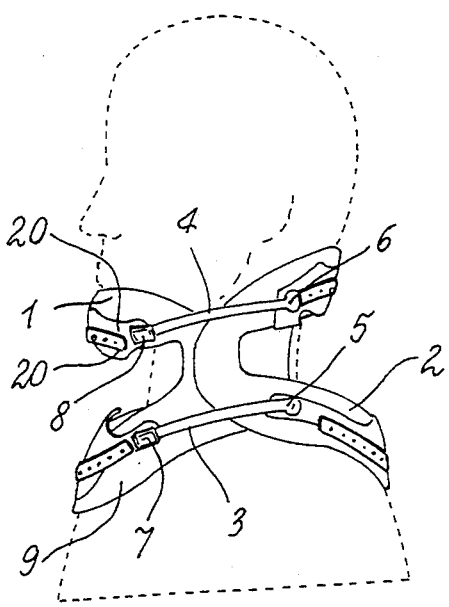
FIG. 3 is a side view of the cervical orthosis positioned onto a head and shoulders portion of a wearer shown in phantom showing the rear and front parts illustrated in FIGS. 1 and 2 and connected with each other with turnbuckles.
Figure 6:
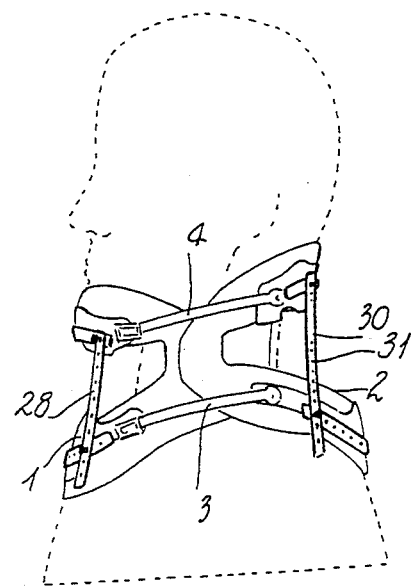
FIG. 6 is a side view of the orthosis similar to the side view of FIG. 3 and additionally illustrating both rear and front adjustment bars to assist further in the holding of the rear and the front of the head in its appropriate elevated position.

Referring now more particularly to the accompanying drawings, the cervical orthosis comprises a front plastic support or semi-component 1 (FIG. 2) for supporting the front portion of a person's head and a rear plastic or semi-component support 2 (FIG. 1) for the rear portion of a person's head, which is shown in phantom (FIG. 6) to provide a visual perspective view. A pair of lower turnbuckles 3 are provided to connect lower portions of supports or semi-components 1 and 2, and a pair of upper turnbuckles 4 are provided to connect the upper portions of supports or semi-components 1 and 2, and they are preferably provided on opposites of the profile portion of the wearer as shown (FIG. 3).

The back or rear semi-component 2 includes a lower articulation sector or pivot connection 5 and an upper articulation sector or pivot connection 6, for mounting one end of turnbuckles 3 and 4, respectively. The other end of turnbuckles 3 and 4 are anchored at lower stop point or connection point 7 and upper stop point or connection point 8 on the front component 1.

Figure 4:
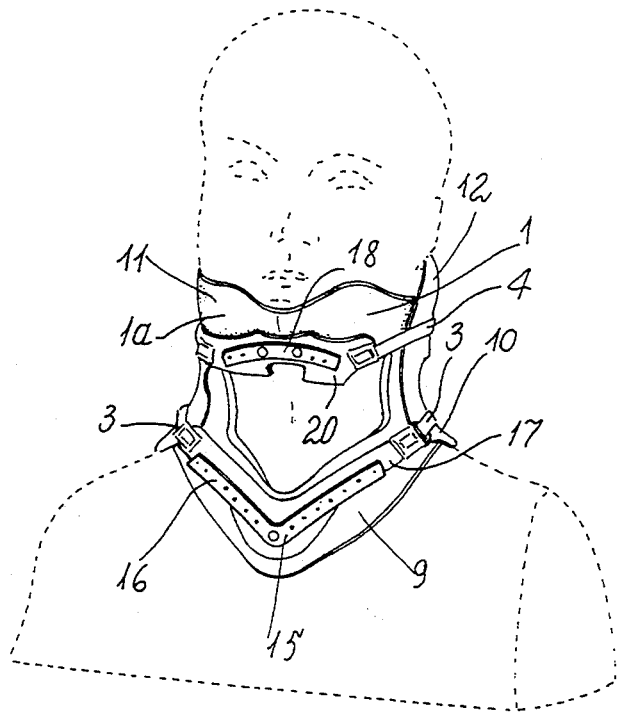
FIG. 4 is a front view of the cervical orthosis positioned onto a head and shoulders of the wearer shown in phantom as illustrated in FIG. 3 and as viewed on the wearer with the front of the head and chin maintained in a preselected position above the shoulders.

As best seen in FIG. 4, at a thoracosternal position a thoracosternal member 9 and at a dorsal position a dorsal member 10 are anatomically shaped, respectively, to fit in their respective positions, and the members at the thoracosternal and dorsal positions create a stable base for each support device that is applied to block the upper part in an appropriate position. The upper part of semi-components 1 and 2 are provided with sectors or casing structures 1a and 2a located in the mentum position 11 and the nape position 12, respectively. Semi-component 1 includes flexible side 14 and semi-component 2 includes flexible side 13. Both semi-components 2 and 1 are joined on their sides by their respective flexible sides 13, 14.

Casing structure or sector 1 and 2 are positioned at the mentum position 11 and nape position 12, respectively.

Figure 7:
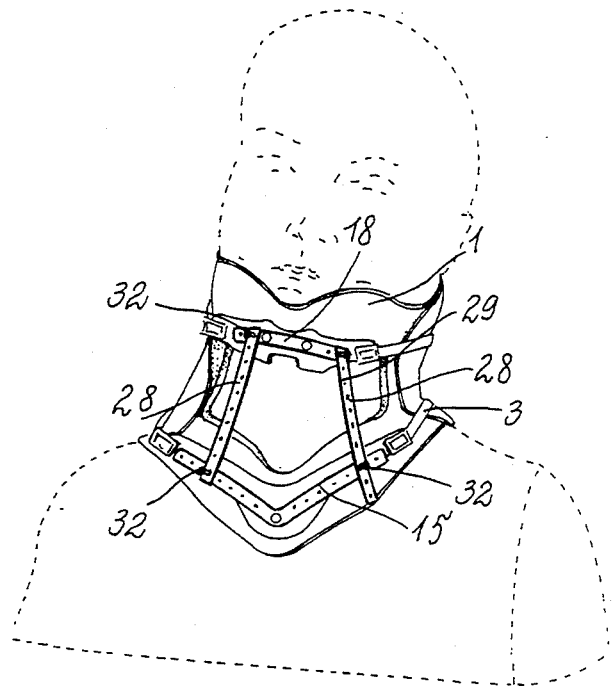
FIG. 7 is a front view of the orthosis showing the relative position of the pair of front adjustment bars which extend in a vertical direction and further assist in holding the front of the head in the appropriate elevated position relative to the shoulders of the wearer.

A lower metallic element 15 (FIGS. 4 and 7) is fixed on a rigid frame 17 in the thoracosternal position 9 and is provided with a scale or adjustment mechanism in the form of holes 16. In the upper part or sector 1a, a partially curved or arc-shaped element 18, is fitted in or onto a rigid plastic element 20, and element 20 also includes at its ends the connection or stop point 8. Element 18 is also provided with an adjustment mechanism in the form of a scale formed by holes 19 aligned symmetrically along the length extent of element 18.

Figure 5:
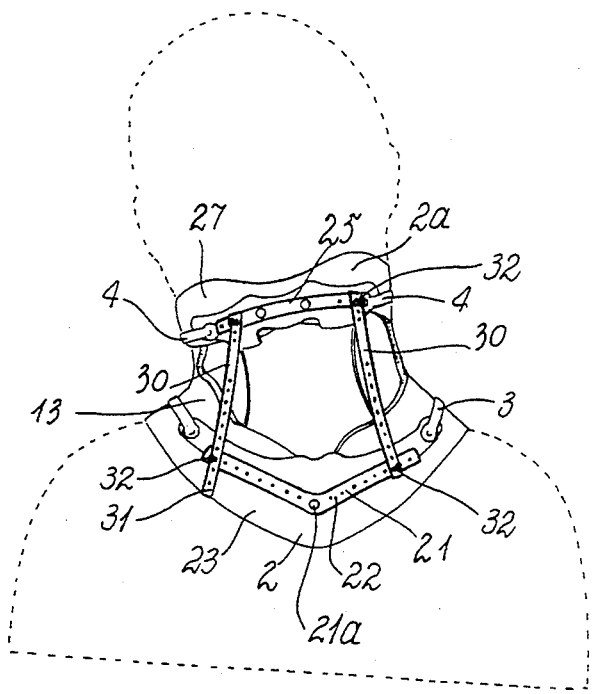
FIG. 5 is a rear view of the cervical orthosis as illustrated in FIGS. 3 and 4 illustrating two flexible side and rear adjustment arms to maintain the side portions between the rear of the head in an appropriate elevated position raised above the back portion of a wearer.

The rear or back portion of the orthosis as best seen in FIG. 5 is provided at the dorsal position 10 with a lower V-shaped element 21 and an upper partially downwardly curved element 25 bent in a direction downwardly toward element 21. A rigid plastic shape 23 is provided on which element 21 is fixed. A scale or adjustment mechanism in the form of holes 22 is provided for adjustment purposes. The holes 22 are uniformly distributed on each side of an indicia as defined by a vertex 21a substantially midway between the ends of the upwardly facing V-shaped element 21 for alignment with the center of an individual's back vertically.

For the rear portion of the individual's head, as best seen in FIG. 5, the upper rear element 25 which is downwardly bent from above includes the upper element 6 for pivotal connection of the upper turnbuckles 4 to the front upper element 20. Rear element 25 includes an adjustment mechanism in the form of holes 26 and element 25 is fitted in a rigid plastic shape 27.

To provide for the appropriate separation of the lower V-shaped bars 15 and 21 from the upper downwardly bent bars 18 and 25, respectively, a pair of front vertical adjustment bars 28 (FIGS. 6 and 7) are connected with bars 15 and 21 and a pair of rear adjustment bars 30 (FIGS. 5 and 6) are connected with the rear lower bar 21 and upper bar 25, respectively.

Bars 28 and 30 are assembled on the front or thoracosternal position 9 and the rear or dorsal position 10, respectively. Bars 28 and 30 are each provided with an adjustment mechanism in the form of holes 29 and 31, respectively. The adjustment holes 29, 31 permit the spacing between the upper and lower elements 15, 18 and 21, 25 to be appropriately adjusted and spaced. Conventional grub screws 32 are provided to lock the two bars 28 to elements 15 and 18 and the two bars 30 to elements 21 and 25, and the holes of the corresponding regulation or adjustment scales are set in symmetry and are locked together by means of the grub screws 32.

Figure 8:
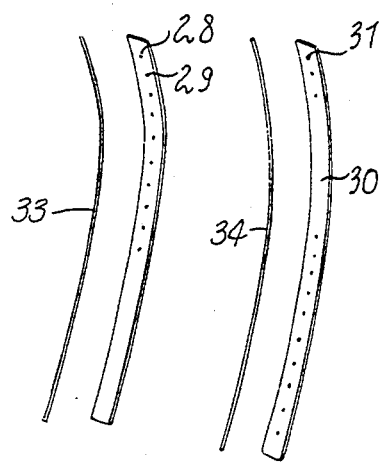
FIG. 8 is a partial view of the vertical adjustment bars which maintain the proper separation between the upper and lower front and rear adjustment bars.

Bars 28 and 30 as shown in FIG. 8 have been bent inwardly at 33 and 34, respectively, to allow the shape of the orthosis to match with the conformation of the thoracosternal and dorsal parts 9 and 10, respectively, at the thoracosternal position and dorsal position, respectively, and at the casing structures 11 and 12 at the mentum and nape positions, respectively.

While only two front bars 28 and two rear bars 30 are shown for purposes of explanation, it will be evident that for a finer adjustment and control of the head position relative to the shoulders additional bars 28 and 30 can be provided.

DESCRIPTION OF OPERATION

The cervical orthosis with multiplanar adjustment is provided with the plastic foam support structure, shaped properly and appropriately, to manage an anatomical support, and it is assembled by setting the front semi-component 1 and the rear semi-component 2. Both of the components are blocked in place using a couple or pair of turnbuckles 3 and 4 which have each one end starting from articulation sectors 5 and 6 of the back semi-component 2. Both turnbuckles are adapted to be anchored in stop points 7 and 8 of the front semi-component.

The semi-components 1 and 2 are anatomically shaped to fit in the thoracosternal position 9 and in the dorsal position 10, respectively. These semi-components 1 and 2 provide a stable base for the support devices that are applied to block the upper part in its appropriate position. The upper part includes sectors located in the mentum position 11 and the nape position 12, respectively. Both structural parts are joined on their sides by flexible sides 13 and 14. Two linear frame components, are fitted in the front semi-component 1 to support the casing structure 11, 12. On the lower sector 9 (the thoracosternal position) the V-shaped metallic element 15 is fixed onto rigid frame 17 with hole scales or adjustment means 16 lined up in symmetry. In the upper part on sector 11 the front upper element 18 is fitted in rigid plastic element 20 with the hole scales or adjustment means 19 lined up in symmetry. Also, the back or rear semi-component 2 is fitted in with two different linear and axially integral components of the frame or casing structures 11, 12, in order to support the same structure. On the lower side of the sector 10, V-shaped metallic element 21 is fixed on the rigid plastic shape 23 with the hole scales or adjustment means 22 aligned in symmetry. In the upper side of the sector 12 an element 25 is downwardly bent from above and is fitted in a rigid plastic shape 27 and with its hole scales or adjustment means 26 also in symmetry.

After the orthosis has been carefully adapted to the patient and the patient's cervical spine has been placed into the optimal treatment position, the orthosis is fixed in place by blocking the casing structure 11, 12 on the four supports. These supports can be assembled with a variable length on parts 9, 10. As noted, four bars 28, 30 are shown, but more than four can be used if further adjustment and refinement of control is desired. Two bars 28 are fitted in the front position with the adjustment holes 29 providing the necessary controlled spacing.

The other two bars 30 are rear bars and fitted in the back position with adjustment holes 31 aligned with the adjustment holes 22, 26 in the elements 21 and 26. When the assemblage is carried out, the two bars 28 are fixed and axially connected to the elements 15 and 18, and the two rear bars 30 are fixed and connected to the elements 21 and 25. The holes of the corresponding regulation scales are set in symmetry and are locked using the grub screws 32.

The bars 28 and 30 are first fitted into elements 18 and 25, starting from their first upper hole, and then subsequently they are blocked and locked onto the elements 15 and 21. As noted heretofore, the paired bars 28 and 30 are inwardly bent to provide for the proper contour while the adjustment takes place and to maintain the proper contour after the adjustment.

In the upper side of the sector 12 an element 25 is bent down from above and is fitted in a rigid plastic shape 27 and with the hole scales 26 in symmetry. After the orthosis has been carefully adapted to the patient and his cervical spine has been placed in the optimal treatment position, the orthosis is fixed in place by blocking the casing structure 11, 12 on the four supports. These supports can be assembled with a variable length on parts 9, 10 using the four bars 28, 30 which are fitted in front and rear positions, respectively. When the assemblage is carried out, the two bars 28 are fixed and axially connected to the elements 15 and 18, and the two bars 30 are fixed and connected to the elements 21 and 25. The holes of the corresponding regulation scales are set in symmetry and are locked using grub screws. The bars 28 and 30 are fitted superiorly into the elements 18 and 25, starting from their first upper hole, and inferiorly they are blocked on the elements 15 and 21. The paired bars 28 and 30 have been bent inward to allow the shape of the orthosis to match with the conformation of the parts 9, 10 and 11, 12.

A right or left inclination of the casing structure can be achieved by blocking the front bar 28 in a different position related to the other front bar, and by carrying out the same adjustment with the back bars 30. The transverse support joint, which can be translated on guides and blocked in two different positions, can carry out the frame support system. The torsional rigidity of the orthosis, as noted heretofore, can also be increased by using two additional pairs of small bars.

While there have been shown what is considered to be the preferred embodiments of the invention, various changes and modifications may be made without departing from the scope of the invention.

I claim:

1. A cervical orthosis, comprising:
    a first semi-component for a thoracosternal position and a second semi-component for a dorsal position;
    each of said semi-components including a lower and an upper part;
    a pair of upper and lower connection means for connection of said upper parts and said lower parts of said semi-components;
    said connection means including means on at least one of said upper and said lower parts for connection of said semi-components;
    spacer means for connecting said lower and upper parts and for appropriately spacing said lower and upper parts of each of said semi-components from each other; and
    adjustment means on said lower parts on each side of an indicia for connection with said spacer means.

2. The orthosis as claimed in claim 1, wherein each of said lower parts includes a V-shaped connector having a vertex at a V-joinder forming said indicia and said spacer means includes two spacers for each of said lower parts, and one of said two spacers being on one side of said vertex and the other of said two spacers being on another side of said vertex.

3. The orthosis as claimed in claim 1, wherein each of said lower parts includes a V-shaped element upwardly opening toward said upper part, and said adjustment means includes adjustable connection means on each of said upwardly opening V-shaped elements and said upper part for connection with said spacer means.

4. The orthosis as claimed in claim 1, including plastic foam structure shaped to form an anatomic support, and said semi-components being set onto said foam structure.

5. The orthosis as claimed in claim 1, wherein said connection means includes pivotal means for connection to one of said upper and lower parts.

6. The orthosis as claimed in claim 1, wherein said connection means includes a pair of turnbuckles for each of said lower parts and said upper parts of said semi-components, and one end of each said turnbuckles including a pivotal connection means for connection thereof to one of said semi-components, and another end of each of said turnbuckles including adjustable connection means for connection to the lower and upper parts of the other of said semi-components.

7. The orthosis as claimed in claim 6, including stop points for anchoring the turnbuckles to one of said front and rear semi-components.

8. The orthosis as claimed in claim 1, wherein said semi-components are anatomically shaped to fit in a thoracosternal position and in a dorsal position.

9. The orthosis as claimed in claim 1, wherein each of said semi-components include integral therewith flexible sides for joining said upper and said lower parts of each of said semi-components.

10. The orthosis as claimed in claim 1, wherein each of said semi-components includes an upper and lower rigid frame and said upper and said lower parts are fixed on said rigid frame.

11. A cervical orthosis, comprising:
    a first semi-component for a thoracosternal position and a second semi-component for a dorsal position;
    each of said semi-components including a lower and an upper part wherein each said upper part includes a partially downwardly curved upper element, and each said lower part includes a V-shaped element upwardly opening toward said downwardly curved element;
    a pair of upper and lower connection means for connection of said upper parts and said lower parts of said semi-components;
    said connection means including means on at least one of said upper and said lower parts for connection of said semi-components;
    spacer means for connecting said lower and upper parts and for appropriately spacing said lower and upper parts of each of said semi-components from each other; and
    adjustable connection means on each of said upwardly opening V-shaped elements and said downwardly curved upper elements for connection with said spacer means.

12. The orthosis as claimed in claim 11, wherein each of said V-shaped elements and said partially downwardly curved upper elements includes adjustment scales, and said spacer means includes adjustment bars having means at each end for connection to said adjustment scales for imparting torsional rigidity to the orthosis.

13. The orthosis as claimed in claim 12, wherein said means at each of said adjustment bars includes holes, and said adjustment scales on said upper and lower elements include holes for alignment with said holes in said adjustment bars.

14. The orthosis as claimed in claim 13, including grub screws for connection of said bars and said upper and said lower elements.

15. The orthosis as claimed in claim 13, wherein said adjustment bars are inwardly bent to conform to the dorsal and thoracosternal portions and the upper and lower casing structure at the mentum and nape positions.

16. The orthosis as claimed in claim 11, including plastic foam structure shaped to form an anatomic support, and said semi-components being set onto said foam structure.

17. The orthosis as claimed in claim 11, wherein said connection means includes adjustment means for connection to one of said upper and said lower parts to provide for multiple individual use, and a pair of turnbuckles for each of said lower parts and said upper parts of said semi-components, and one end of each of said turnbuckles including a pivotal connection means for connection thereof to one of said semi-components, and another end of each of said turnbuckles including adjustable connection means for connection to the lower and upper parts of the other of said semi-components.

18. The orthosis as claimed in claim 17, including stop points for anchoring the turnbuckles to one of said front and rear semi-components.

19. A cervical orthosis, comprising:
a first semi-component for a thoracosternal position and a second semi-component for a dorsal position;
each of said semi-components including a lower and an upper part;
a pair of upper and lower connection means for connection of said upper parts and said lower parts of said semi-components;
means on at least one of said upper and said lower parts for connection of said semi-components;
a pair of turnbuckles for each of said lower parts and said upper parts of said semi-components, and one end of each of said turnbuckles including a pivotal connection means for connection thereof to one of said semi-components, and another end of each of said turnbuckles including adjustable connection means for connection to the lower and upper parts of the other of said semi-components; and
spacer means for connecting said lower and upper parts and for appropriately spacing said lower and upper parts of each of said semi-components from each other.

20. The orthosis as claimed in claim 19, including stop points for anchoring the turnbuckles to one of said front and rear semi-components.

* * * * *